(12) United States Patent
Konowalchuk et al.

(10) Patent No.: US 7,045,548 B2
(45) Date of Patent: May 16, 2006

(54) METHODS OF INACTIVATING VIRUSES

(75) Inventors: Thomas W. Konowalchuk, Newport, OR (US); Jack Konowalchuk, Newport, OR (US)

(73) Assignee: Life Force Technologies, Inc., Newport, OR (US)

( * ) Notice: Subject to any disclaimer, the term of this patent is extended or adjusted under 35 U.S.C. 154(b) by 0 days.

(21) Appl. No.: 10/016,189

(22) Filed: Dec. 6, 2001

(65) Prior Publication Data

US 2002/0165278 A1    Nov. 7, 2002

Related U.S. Application Data

(63) Continuation-in-part of application No. 09/795,279, filed on Feb. 28, 2001.

(51) Int. Cl.
*A01N 37/00*     (2006.01)
*A01N 31/00*     (2006.01)
(52) U.S. Cl. ...................................... 514/557; 514/739
(58) Field of Classification Search ................ 514/739, 514/557
See application file for complete search history.

(56) References Cited

U.S. PATENT DOCUMENTS

| | | | |
|---|---|---|---|
| 4,513,008 A | 4/1985 | Revici et al. ................ | 514/560 |
| 4,647,458 A | 3/1987 | Ueno et al. | |
| 4,975,217 A | 12/1990 | Brown-Skrobot et al. .. | 252/107 |
| 5,043,357 A | 8/1991 | Hoffler et al. ............... | 514/553 |
| 5,071,650 A | 12/1991 | Dove et al. ................. | 424/85.8 |
| 5,385,938 A * | 1/1995 | Yu et al. | |
| 5,405,602 A * | 4/1995 | Simmons et al. | |
| 5,512,200 A | 4/1996 | Garcia ......................... | 252/142 |
| 5,531,984 A | 7/1996 | Staats ........................ | 424/78.07 |
| 5,534,554 A | 7/1996 | Katz et al. ................... | 514/724 |
| 5,728,404 A | 3/1998 | von Rheinbaben et al. . | 424/642 |
| 5,767,163 A | 6/1998 | Kundsin ...................... | 514/642 |
| 5,952,392 A | 9/1999 | Katz et al. ................... | 514/724 |
| 6,034,133 A | 3/2000 | Hendley ...................... | 514/573 |

FOREIGN PATENT DOCUMENTS

| | | | |
|---|---|---|---|
| CA | 1221640 | 5/1987 | ................. 167/283 |
| GB | 2187097 | 9/1987 | |
| WO | WO 00/62613 | 10/2000 | |

OTHER PUBLICATIONS

Wenninger, International Cosmetic Ingredient Dictionary and Handbook, 7th ed., vol. 1, p. 163-168.*
Therapeutic Products Programme Guidelines published by Health Canada, Apr. 1999, pp. 42-45.*
Remington's Pharmaceutical Sciences, 18th ed., 1990, pp. 218-219 and 1314-1315.*
Merck Index, 11th ed., 1989, Glycolic acid monograph 4394, p. 4399.*
Milton B. Dobkin, et al., "Virucidal Efficacy of Saturated Intermediate Length Straight-chain Alcohols in Biologically Active Protein Solutions," *Biologicals* (1991) 19: 177-185.
S.S. Bhatia and J.P. Soman, *Indian Journal of Animal Sciences* (1997) 68(6): 518-520.
G. Poli, et al., "Virucidal Activity of Organic Acids", *Food Chemistry*, (1979) 4: 250-258.
Wallace Snipes, et al., "Inactivation of Lipid-Containing Viruses by Long-Chain Alcohols," *Antimicrobial Agents and Chemotherapy* (1977) 11: 98-104.
Jack Konowalchuk, Joan I. Speirs, "Virus Inactivation by Grapes and Wines," *Applied and Environmental Microbiology* (1976) 32: 757-763.
European Search Report, Feb. 15, 2004.

* cited by examiner

*Primary Examiner*—San-Ming Hui
(74) *Attorney, Agent, or Firm*—Quine I.P. Law Group, P.C.; Tom Hunter

(57) ABSTRACT

A method of inactivating viruses comprises contacting the virus with a virucidally effective amount of a composition consisting essentially of a C1 to C3 monohydroxy alcohol or a C2 to C4 diol and a sufficient amount of an acid to adjust the pH of the composition to below 4.6. Topical administration of the composition is preferred and is effective in treating lesions associated infections by viruses such as herpes simplex. Nasal deliverable forms are effective in treating symptoms due to viruses that cause the common cold. Pharmaceutical compositions for use in the present method are provided.

29 Claims, No Drawings

METHODS OF INACTIVATING VIRUSES

CROSS-REFERENCE TO RELATED APPLICATIONS

This application is a Continuation-in-Part application of U.S. patent application Ser. No. 09/795,279, filed Feb. 28, 2001, and entitled "Virucidal Compositions."

BACKGROUND OF THE INVENTION

1. Field of the Invention

The present invention relates to virucidal compositions for the treatment and/or prevention of superficial lesions or sores, including canker sores and lesions caused by viruses of the Herpesviridae and Poxviridae families, and for the treatment and/or amelioration of symptoms caused by the common cold.

2. Description of the Prior Art

Pathogenic viruses can be classified into two general types with respect to the viral structure, i.e., those that contain lipids and those that do not. Some well known lipid-containing pathogenic viruses, known as "enveloped" viruses, include herpes virus, e.g., herpes simplex 1 and 2; myxovirus, e.g., influenza virus; paramyxovirus, e.g., virus responsible for measles and mumps, and respiratory syncitial virus responsible for croup; corona virus, which is also implicated in the common cold; and toga virus, e.g., rubella virus and virus responsible for encephalitis and hemorrhagic fever. Many other pathogenic viruses lack an outer envelope, and therefore are characterized as "naked" viruses. Included in this category are the rhinovirus (the principle causative agent of the "common cold"), influenza viruses, polioviruses, and adenoviruses.

Viral infections cause considerable discomfort, disease and can be fatal. Viruses such as cytomegalovirus (CMV), human lymphotrophic viruses (e.g., HTLV-1) and human immunodeficiency viruses (e.g., HIV-1) result in significant morbidity and mortality. Herpes simplex viruses (HSV-1 and HSV-2) are associated with inflammation and lesions of the skin and mucosal membranes, including cold sores, fever blisters and genital herpes lesions. Varicella-zoster virus (VZV) causes chicken pox and shingles, and Epstein-Barr virus (EBV) is associated with mononucleosis. Influenza viruses cause flu symptoms and can be fatal. HIV causes acquired immunodeficiency, which debilitates and kills infected individuals. Although these viruses may remain latent in some cells and for varying periods of time, generally viral replication results in irreversible destruction of the infected cell producing different clinical manifestations of the diseases they cause.

Herpes simplex infections occur and recur at many areas and organs of the body, but particularly the skin and mucocutaneous areas. Roughly 50 million Americans suffer from fever blisters or cold sores with more than 100 million episodes estimated annually. The medical term for the condition is recurrent herpes simplex labialis. It is caused by the herpes simplex virus (HSV) which, following a primary infection, takes up permanent life-long residence and lies dormant in the nerve ganglia. Upon reactivation by various stimuli, the virus travels along nerve pathways towards the lips and mouth where it emerges as a lesion or blister. The disfiguring lesions typically last 7 to 10 days. Other common sites for outbreaks caused by HSV include anywhere on the skin such as the ears, nose, chest, abdomen, arms, palms, dorsa of the hands, fingers, thighs and legs. Other common sites are the eyes and cervix. Less often involved but observed are the mouth, respiratory tract and central nervous system.

The "common cold" is a phrase used by both physicians and lay persons alike for the identification of acute minor respiratory illness. Since the identification of rhinovirus in 1956, a considerable body of knowledge has been acquired on the etiology and epidemiology of common colds. It is known that the common cold is not a single entity, but rather is a group of diseases caused by members of several families of viruses, including parainfluenza viruses, rhinoviruses, respiratory syncytial viruses, enteroviruses, and coronaviruses. Much work has been performed in characterizing viruses that cause the common cold. In addition, the molecular biology of rhinoviruses, the most important common cold viruses, is understood in great detail. In contrast, progress on the treatment of common colds has been slow despite these advances. While there are now large numbers of compounds that have been found to exhibit antiviral activity against cold viruses in cell culture, many antiviral compounds have had limited effectiveness in patients.

Because of the widespread dissatisfaction with the currently marketed treatments for the common cold and allergic rhinitis within the affected population, there exists a need for a more efficacious and safe treatment. The present invention provides such a treatment.

It is known in the art that quaternary ammonium compounds such as benzalkonium chloride are effective against bacteria but are not virucidal. In Hendley, et al., (*Antimicrobial Agents and Chemotherapy*, 14:690–694 (1978)) foams containing ethyl alcohol, benzalkonium chloride (BAK), and hexachlorophene were evaluated. Ethyl alcohol alone was not effective, and the combination of ethyl alcohol with BAK was fairly ineffective in killing rhinoviruses.

It is known in the art that "enveloped" viruses are relatively sensitive and, thus, can be inactivated by virucidal disinfectants known so far. In contrast, greater problems are caused by naked viruses, which are substantially more stable against conventional disinfectants and which can be inactivated only with relatively high concentrations of formaldehyde. However, formaldehyde is undesirable because of toxicity and does not allow the disinfection of contaminated parts of the body to be effected in either the clinic or the laboratory.

Poli, et al. (*Food Chem.* (England) 4(4):251–258 (1979)) describe a study of the virucidal action of organic acids (citric, malic, etc.). These workers found that citric, malic, pyruvic and succinic acids, among others, were effective in vitro against "enveloped" viruses (herpesvirus, orthomyxovirus and rhabdovirus (Rabies virus)). Their experiments were carried out at room temperature with aqueous solutions of pure acids. No substrate or carrier was used. The three viruses chosen for study by these workers were all "enveloped" viruses. Poli, et al. also observed that these acids were not effective against adenovirus, which is a "naked" virus. Based on this, they concluded that these acids were effective in vitro against "enveloped" viruses but not against "naked" viruses. In vivo, an acid solution would not work, as it is unable to penetrate the outer dermal layer and so cannot get to the virus where it is replicating.

The use of certain alcohols (i.e., alcohols of certain chain lengths) to inactivate lipid-containing viruses is disclosed by W. Snipes, et al. (*Antimicrobial Agents and Chemotherapy*, 11(1): 98–104, (1977)). Although the authors used alcohols ranging from C4 to C18, they point out that a striking peak in virucidal activity was found for saturated alcohols having chain lengths from ten to fourteen carbons. Since longer-chain alcohols having ten carbons or more are extremely insoluble in aqueous media, the preferred C10–C14 alcohols first had to be prepared in 95% ethanol at 100 times the desired final concentration. The final treatment was in solutions adjusted to a pH of at least 7.2. Thus, although the C10 to C14 alcohols were shown to have good virucidal action, their relatively low water solubility is a disadvantage in view of the initial preparation steps required.

Konowalchuk, et al. reported a 1000-fold reduction in poliovirus infectivity after incubation with grape juice, at the natural pH of the wine (pH 3.3–4.4) or at pH 7.0 for 24 hours at 4° C., and found that commercial grape juice at neutral pH inactivated the herpes simplex virus. Red wines were reported to be more antiviral than white wines. The effect of wine at its natural pH against the herpes simplex virus was not examined.

Noda, et al. (*J. Jap. Ass. Infect. Dis.* 55:355–366 (1981)) have reported that pure methanol, ethanol, n-propanol, isopropanol or butanol have distinct but limited virucidal effects in vitro in very high concentrations of around 80% or more. Lower concentrations of these alcohols were not sufficiently effective. Individually, pure propanol, isopropanol, or various butanols were not sufficiently active against "naked" hydrophilic viruses. Known mixtures of ethanol and isopropanol with a total active-substance content of 20 to 40% also show no virucidal activity.

Von Rheinbaben, et al. (U.S. Pat. No. 5,728,404) disclose compositions having virucidal activity against "naked" viruses (e.g., polio, adeno, vaccina, and SV40 tumor virus) comprising 50% to 90% by weight of at least one member selected from the group consisting of $C_1$–$C_4$ aliphatic monohydric alcohols and from 0.1% to 1.0% by weight of at least one metal salt, such as a zinc salt. Von Rheinbaben et al. found that compositions comprising between 40–80% by weight of ethanol, n-propanol, isopropanol, butanol, or mixtures thereof were ineffective against polio, adeno, vaccinia, and SV40 tumor viruses; however, these compositions could be made virucidal by adding metal salts to these alcoholic compositions.

Revici, et al. (U.S. Pat. No. 4,513,008) disclose a method of inactivating an enveloped virus (HSV-2) which comprises contacting the virus with a virucidally effective amount of a C20 to C24 linear polyunsaturated acid, aldehyde or primary alcohol having 5–7 double bonds.

Brown-Skrobot, et al. (U.S. Pat. No. 4,975,217) disclose a composition having germicidal activity when applied to hands contaminated with *Serritia marcescens*, a gram-negative bacteria, wherein the composition consists essentially of an anionic surfactant (e.g., an alkyl sulfonate salt) and an organic acid (malic acid, citric acid, and mixtures thereof). Brown-Skrobot, et al. state that the surfactant alone and the acid alone showed no germicidal activity, and emphasize that both the organic acid and the anionic surfactant must be used to achieve significant germicidal activity. Alcohol was mentioned as an optional ingredient in the Brown-Skrobot, et al. composition. However, Brown-Skrobot, et al., did not test the effectiveness of this composition against viruses.

Hoffler, et al. (U.S. Pat. No. 5,043,357) disclose compositions having virucidal activity against naked viruses (e.g., poliovirus type 1), having at least 70% by weight of ethanol and/or propanols and from 0.5% to 5% by weight of a short-chain acid. Ethanol and propanol alone did not exhibit sufficient activities against the naked viruses. These compositions were not tested for their effectiveness against enveloped viruses, nor were the virucidal activities of the compositions tested in vivo.

Hendley, et al. (U.S. Pat. No. 6,034,133) disclose a hand lotion effective against the naked rhinovirus, containing malic acid, citric acid, and a C1 to C6 alcohol for preventing hand-to-hand transmission to rhinoviruses. Hendly, et al. state that the lotions retain their virucidal activity as long as the concentration of the alcohol in the lotion is between 25–90%. The pH of the lotion is adjusted to be between pH 3 and pH 6 to avoid irritating the skin.

Dove, et al. (U.S. Pat. No. 5,071,650) disclose an in vitro method of inactivating viruses such as VSV (a lipid-coated virus) present in a aqueous solution of biologically active protein (e.g., plasma or cell cultures) by treating the solution with an intermediate length alcohols (C4 to C10) at a pH of about 4 to 5 at a temperature of 4° C., with virucidal activity increasing with increasing carbon chain length up to C8. Ethanol and butanol were found to be fairly inactive under these conditions.

Recently, the FDA has approved docosanol (10% cream) as a treatment for recurrent oral-facial herpes (cold sores and fever blisters) (see Katz, et al., U.S. Pat. Nos. 5,952,392 and 5,534,554). Because of the low water solubility of this long chain (C26) alcohol, the composition requires a difunctional block-polymer nonionic surfactant in order to produce a suspension or emulsion of the docosanol. Further, U.S. Pat. No. 5,534,554, states that certain excipients were detrimental to the activity of n-docosanol, and stress that the preparation of stable, effective n-docosanol-containing compositions presented an unexpectedly difficult challenge.

A need continues to exist for topical compositions that are active against enveloped and naked viruses and have very low toxicity. In particular, there is a need for topical virucidal compositions that are effective against viruses of the Herpesviridae and Poxviridae families that are inexpensive and easy to use.

SUMMARY OF THE INVENTION

These and other needs are satisfied by the present invention, which provides virucidal compositions that are highly effective over a broad spectrum of viruses and yet can be produced and used with safety.

More specifically, this invention provides a method utilizing topical compositions of this invention for the treatment and/or prevention of canker sores and lesions caused by viruses that reside in and/or are transmitted by and/or infect the cells of the dermis or epidermis. Examples of such viruses include those of the Herpesviridae and Poxviridae families. The compositions of this invention are suitable for topical applications, such as to the lips in treatment of cold sores and canker sores, to the skin for the treatment of Herpes infections and to the surrounding skin of the penis, vagina, or rectum for treatment and prevention of infections caused by such viruses. The compositions of this invention may also be applied to other parts of the organism, for example to the oral, vaginal and rectal cavities, as well as surrounding tissue.

This invention further provides compositions which may be used in fluids used to kill viruses on instruments and surfaces such as examining tables, gloves, towels and other surfaces which might come in contact with the animal or human body during the course of medical and dental examinations, and as safe anti-viral disinfectants in a clinical environment. Such compositions can be contained in aerosol cans for spray delivery of the compositions.

This invention further provides compositions effective against viruses that cause the common cold, such as rhinoviruses, adenoviruses, enteroviruses, cornoviruses, respiratory syncytial viruses, influenza viruses and parainfluenza viruses.

Accordingly, one aspect of this invention provides virucidally effective compositions consisting essentially of an aqueous solution of a short chain alcohol or diol adjusted to a pH at or below 4.6 with a suitable acid. Such compositions suitable for topical application and nasal deliverable form are also provided.

In another embodiment, this invention provides a method of inactivating viruses, which comprises contacting the site of the virus or the virus itself with a virucidally effective amount of a composition of this invention.

In another embodiment, this invention provides a method of treating lesions associated with a viral infection such as a herpes infection in an animal or human subject, which comprises applying to the affected area an amount of a virucidal composition of the invention effective for reducing or arresting such lesions.

In another embodiment, this invention provides a method of preventing lesions associated with viral infections such as a herpes infection in an animal or human subject, which comprises applying to an area of the skin an amount of a virucidal composition of the invention effective for preventing formation of such lesions.

Additional novel features and advantages of this invention shall be set forth in part in the description that follows, and in part will become apparent to those skilled in the art upon examination of the following specification or may be learned by the practice of the invention. The advantages and novel features of this invention may be realized and attained by means of the instrumentalities, combinations, and methods particularly pointed out in the appended claims.

DETAILED DESCRIPTION OF THE INVENTION

The present invention provides compositions having virucidal activity that are suitable for the treatment and/or prevention of lesions caused by viruses that reside in and/or are transmitted by and/or infect the cells of the dermis or epidermis. Examples of such viruses include those of the Herpesviridae family such as herpes simplex virus, varicella-zoster virus, cytomegalovirus, and Epstein-Barr virus, and viruses of the Poxviridae family such as molluscum contagiosum. The compositions are also effective against canker sores. Herpes simplex refers to a variety of infections caused by herpesvirus types 1 and 2. Type 1 infections are marked most commonly by the eruption of one or more groups of vesicles on the vermilion border of the lips or at the external nares, and type 2 infections are marked by such lesions on the genitalia.

More specifically, the present invention provides topical compositions for preventing or reducing canker sores, or viral lesions associated with infections from viruses of, for example, the Herpesviridae family or the Poxviridae family, or for shortening the time of healing of such sores or lesions.

This invention further provides virucidal compositions effective against viruses that causes the common cold, such as rhinoviruses, adenoviruses, enteroviruses, comoviruses, respiratory syncytial viruses, influenza viruses and parainfluenza viruses. Such compositions can be provided in any number of forms, such as nasal deliverable forms.

The compositions of this invention consist essentially of a dilute aqueous solution of a C1 to C3 monohydroxy alcohol or a C3 to C4 diol which has been adjusted to a pH of 4.6 or below by the addition an inorganic or an organic acid. As used herein, "C1,""C2,""C3," and "C4" refer to alcohols having one, two, three, or four carbons, respectively. Such alcohols may be straight chain or branched alcohols. In one embodiment, the compositions are buffered, preferably with a suitable buffer that will maintain the pH of the composition. Such buffers are well known to persons skilled in the art.

In preferred embodiments, the compositions comprise aqueous solutions having between about 0.2% and 13% by volume of the alcohol. More preferably, the compositions comprise between about 5% and 10% by volume of the alcohol in water. Suitable alcohols include short chain alcohols and diols, including methanol, ethanol, n-propanol, 2-propanol, 1,2-propanediol, 1,3-propanediol, 1,2-butanediol, 1,3-butanediol, 1,4-butanediol, and 2,3-butanediol.

Organic acids which may be used in the compositions of this invention include, but are not limited to acetic, citric, glutaric, glycolic, lactic, malic, succinic, and valeric acids. Preferably the organic acid is glycolic acid.

Inorganic acids which may be used in the compositions of this invention include, but are not limited to, hydrochloric, chlorous, sulfuric, hypochlorous, hypophosphorous, iodic, nitrous, periodic, phosphoric, phosphorous, and sulfurous acids. Preferably the inorganic acid is hydrochloric acid.

In one embodiment, a composition of this invention consists essentially of 10% by volume of 95% ethanol in water, wherein the pH of the composition is adjusted to a pH of 4.6 or below by the addition of glycolic acid or HCl. For example, the pH may be adjusted to 4.6 by the addition of a 0.6% aqueous glycolic acid solution or a 0.1M HCl solution.

The compositions of the present invention contain ingredients, i.e., an alcohol and an acid, which individually are not potent antivirals when applied topically to a site of infection. For example, it is known that certain organic acids such as dicarboxylic acids are virucidal in vitro but are ineffective when applied topically. In addition, lower chain alcohols such as ethanol and propanol are known to be ineffective against enveloped viruses both in vitro and in vivo. Surprisingly, however, a synergistic antiviral effect is noted when these ingredients (i.e., an organic or inorganic acid and a C1, C2, or C3 alcohol or a C2, C3, or C4 diol,) are used in combination in the compositions of this invention. For example, it was surprisingly discovered that when an effective amount of a virucidal composition of this invention having a pH at or below 4.6 was topically applied to a lesion or to the site of a potential lesion caused by a virus such as HSV-1, the virus was substantially inactivated, thereby interrupting and preventing the spread of the virus.

Thus, it was surprisingly and unexpectedly discovered that dilute aqueous compositions comprising short chain alcohols used in combination with an organic or inorganic acid, wherein the acid is added in an amount that adjusts the pH of the composition to a pH of 4.6 or below, provide effective topical virucidal compositions. This is in contrast to the teachings of the prior art, which indicate that either an intermediate or long chain length alcohol (i.e., C8 to C26) and/or high concentrations of the alcohol (especially in the case of short chain alcohols) is required for virucidal activity.

In one example, the topical compositions of this invention were found to be active in vivo against HSV-1 (causing cold sores and fever blisters), HSV-2 (causing genital herpes) and herpes zoster (causing shingles). However, it is believed that these compositions will be active against other viruses in the Herpesviridae family, which are similar in structure or mechanism of infection, including the varicella virus (causing chicken pox). Evidence of the efficacy of the virucidal compositions of the invention against HSV-1 both in vitro and in vivo has been obtained using standard assay procedures as described below in the Examples.

Table 1 shows of time required for growth inhibition of herpes simplex virus 1 (HSV-1) using various concentrations of aqueous ethanol solutions adjusted to pH 3.5 by the addition of 0.1N or 1.0N HC1, both when the solutions were not diluted and after diluting the solutions by ¼, 1/16, or 1/64 with Eagles medium. The experiments were performed as described in Example 1.

TABLE 1

| % Ethanol | 5 minute exposure | | | | 10 minute exposure | | | |
|---|---|---|---|---|---|---|---|---|
|  | undiluted | ¼ | 1/16 | 1/64 | undiluted | ¼ | 1/16 | 1/64 |
| 1.0 | + | + | + | + | − | + | + | + |
| 2.5 | + | + | + | + | − | − | + | + |
| 5.0 | + | + | + | + | − | − | + | + |
| 10 | + | + | + | + | − | − | + | + |
| 12.5 | − | − | + | + | − | − | − | + |

+: Virus growth
−: No virus growth

As shown in Table 1, only the 12.5% ethanol solution inhibited the virus after an exposure time of five minutes. However, when the exposure time was increased to 10 minutes, even fairly dilute compositions (e.g., the 2.5% ethanol solution diluted by ¼) effectively inhibited growth of the virus.

Various aqueous acid solutions were tested for the virucidal activity as shown in Table 2. The glycolic acid solution having a pH of 3.8 was prepared by preparing a 0.6% by weight solution of glycolic acid in water, and the remaining glycolic acid solutions were prepared by adjusting pH of the 0.6% glycolic acid solution by the addition of 0.1N or 1.0N sodium hydroxide. The succinic acid solution was a 0.2% by weight solution of succinic acid in water.

TABLE 2

Effect of pH on the growth of HSV-1 after an exposure of 4 minutes.

| Acid | pH | Virus growth at sample dilution | | | |
|---|---|---|---|---|---|
|  |  | Undiluted | ¼ | 1/16 | 1/64 |
| glycolic acid | 3.8 | − | − | − | − |
| glycolic acid | 4.0 | + | + | + | + |
| glycolic acid | 6.0 | + | + | + | + |
| succinic acid | 4.2 | − | + | + | + |

+: Virus growth
−: No virus growth

In another experiment, various alcohols at concentrations of 0.2% by volume were adjusted to various pH's to determine the upper limit of the pH that is required for each alcohol in order for the acidic alcohol solution to exhibit antiviral activity against HSV-1. Samples of each alcohol at pH 4.0 to 6.8 at increments of 0.2 pH units were incubated with the virus for 2 minutes and then plated as described in Example 1. That is, each of the alcohols in Table 3 were tested at pH 4.0, 4.2, 4.4, 4.6, 4.8, 5.0, 5.2, 5.4, 5.6, 5.8, 6.0, 6.2, 6.4, 6.6 and 6.8. The pH was adjusted using 0.1N or 1.0N HCl. Methanol, n-butanol, and 2,3-butanediol were effective in completely inactivating HSV-1 up to a pH of 4.6. Ethanol was effective up to a pH of 4.4. 1,2-Butanediol was effective up to a pH of 4.2.

TABLE 3

Upper pH limit at which HSV-1 is inactivated by the alcohol

| Alcohol | Concentration of alcohol | Upper limit of pH |
|---|---|---|
| methanol | 0.2% | 4.6 |
| ethanol | 0.2% | 4.4 |
| n-butanol | 0.2% | 4.6 |
| 1,2-butanediol | 0.2% | 4.2 |
| 2,3-butanediol | 0.2% | 4.6 |

It is well known in the art that ethanol or propanols alone have no virucidal activity against enveloped viruses. While not wishing to be bound by any particular theory, it is believed that the alcohol facilitates penetration of the acid through the outer dermal layer to the site of HSV replication. That is, a synergy was observed between the acid and the alcohol, in that it was found that both must be used to achieve significant topical virucidal activity. Further, it was discovered that the pH of the composition determined the virucidal effect of the composition greater than the acid used to lower the pH of the compositions. Thus, the low pH compositions of this invention are better able to penetrate to the deeper, infected layers of the skin better than the individual components alone, thus enhancing the effectiveness of the alcohol and/or the acid to inactive the virus. For example, without the alcohol, the acids may not penetrate the tissue to allow effective action against the virus. It is for the purposes of enhancing the penetration and extending retention time of the acid that the short chain alcohols are used in the virucidal compositions of this invention.

A further advantage of the compositions of this invention is that the short chain alcohols avoid the insolubility problems as well as the unpleasant odors associated with alcohols having longer chain lengths The compositions were evaluated for the treatment of recurrent oral-facial herpes simplex infections as described in Example 2. A group of patients applied a solution consisting essentially of 10% by volume of 95% ethanol and 0.6% by weight glycolic acid in water, adjusted to pH 2.45, at the time of erythema, papule or vesicle stages. Development of blisters was arrested and rapid crusting of the vesicles occurred within 2 to 3 days of treatment, as compared to 10 or more days without treatment. When the same composition was applied within 24 hours of the prodromal stage of infection, that is, during awareness of burning, tingling, or itching but before blister development, the subjects noted that development of a papule did not occur. Thus, the compositions of the invention appear to prevent the formation of lesions, as well as being effective in reducing the healing time of the lesions.

Another patient suffering from recurrent herpes zoster of the face applied a composition of this invention comprising 13.5% ethanol mixed with aqueous glycolic acid to give the composition a pH of 3.1. The composition was applied 3 times in 20-minute intervals. Pain at the site of the lesion subsided immediately after application. The herpes zoster lesion healed in 2 days, in contrast to a previous outbreak in the same patient, which lasted 3 months. Healing time, of course, depends on the size of the lesion. For example, in another zoster patient having a six inch lesion, healing time was about 10 days after the 3 applications at 20-minute intervals, compared to a healing time of 3–6 months without treatment.

While not wishing to be bound by any theory, it is believed that the compositions of this invention remain active for over 24 hours in the dermal/epidernal junctions, and bind to or inactivate the receptor sites to which the virus attaches and/or uses to penetrate the target cell wall. This is based on several observations, including: 1) if a virus penetrates a cell it takes over 24 hours before the cell bursts and releases the virus, and 2) three applications of a composition of this invention at 20 minute intervals was sufficient to arrest development of blisters and to prevent further outbreaks. Thus, the compositions of this invention may also be used as a prophylactic to prevent the spread of a virus between humans. For example, if one partner has an active outbreak caused by HSV-2, the other partner can apply a composition of this invention around the genitals to prevent infection by HSV-2.

The topical virucidal compositions of this invention can be administered singly or as divided dosages throughout the day. For the control of HSV-1 infections, application of a virucidally effective amount of a composition according to the invention to an infected area, e.g., skin surfaces such as the area around the mouth, lips, mucous membranes, eyes, of an animal or human subject suffering from a viral infection, especially a herpes infection, will generally range from about one to three applications per day, for example at 20 minute intervals, depending upon the area to be treated, the severity of the symptoms and the nature of the virucidal agent and the topical vehicle employed. A preferred topical preparation is an acidic alcohol solution wherein about 0.2 to 13% of the alcohol is used per milliliter of water or buffer, wherein the pH of the solution has been adjusted by the acid to a pH at or below 4.5, and preferably to a pH of about 2.6. The compositions of this invention are administered topically to the locus to be protected or treated by immersing, spraying or swabbing said locus.

For the control of genital herpes, i.e., HSV-2 infections, the compositions of this invention are administered intravaginally preferably in admixture with a pharmaceutical carrier. The carrier is, of course, chosen with regard to the intended route and method of administration. In the present invention administration is accomplished topically, i.e., to a definite place or locus, in this instance, for example, the vagina, in the form of a cream, ointment, foam, jelly, tablet, ovule or other suitable composition which lends itself to a topical vaginal dosage form. Creams and ointments are preferred forms.

The compositions of this invention are also suitable for the treatment or amelioration of symptoms caused by a virus responsible for the common cold. Such viruses include rhinoviruses, adenoviruses, enteroviruses, cornoviruses, respiratory syncytial viruses, influenza viruses and parainfluenza viruses. For example, one patient suffering from nasal congestion due to the common cold applied a composition of this invention intranasally and experienced rapid relief of such symptoms.

Such compositions can be provided in any number of forms, such as nasal deliverable forms. To provide ease of use for the patient, the compositions may be provided in a prepackaged kit, which may also contain a spray or dropper device for intranasal delivery of metered doses of combined medications for intranasal use.

One mode of application of the virucidal compositions of the invention is as a topical agent. Preferably, the topical agent is a solution, that is, a liquid formulation comprising the aqueous alcohol and the acid. Other suitable forms include semi-solid or solid forms comprising a carrier indigenous to topical application and having a dynamic viscosity preferably greater than that of water, provided that the carrier does not deleteriously react with the acid or the alcohol in the composition. Suitable formulations include, but are not limited to, lip balms, suspensions, emulsions, creams, ointments, powders, liniments, salves and the like. If desired, these may be sterilized or mixed with auxiliary agents, e.g., preservatives, stabilizers, wetting agents, buffers or salts for influencing osmotic pressure and the like. Preferred vehicles for semi-solid or solid forms topical preparations include ointment bases, e.g., polyethylene glycol-1000 (PEG- 1000); conventional ophthalmic vehicles; creams, e.g., HEB cream; and gels, e.g., K-Y gel; as well as petroleum jelly and the like. These topical preparations may also contain emollients, perfumes, and/or pigments to enhance their acceptability for various usages, provided that the additives do not deleteriously react with the acid or the alcohol in the composition.

Also suitable for topical application are sprayable aerosol preparations wherein the virucidal compound, preferably in combination with a solid or liquid inert carrier material, is packaged in a squeeze bottle or in admixture with a pressurized volatile, normally gaseous propellant, e.g., a Freon (chlorofluorocarbon) or environmentally acceptable volatile propellant. Such compositions can be used for application to environmental surfaces, e.g., examining tables, toilet seats and the like, and/or for application to the skin or to mucous membranes. The aerosol or spray preparations can contain solvents, buffers, surfactants, perfumes, and/or antioxidants in addition to the virucidal compounds of the invention.

The compositions of this invention can be employed in mixture with conventional excipients, i.e., pharmaceutically acceptable organic or inorganic carrier substances suitable for topical application which do not deleteriously react with the acid or the alcohol in the composition. Suitable pharmaceutically acceptable carriers include but are not limited to water, salt solutions, alcohols, vegetable oils, polyethylene glycols, gelatin, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, lubricants, preservatives, stabilizers, wetting agents, emulsifiers, salts for influencing osmotic pressure, buffers, coloring, flavoring and/or aromatic substances and the like which do not deleteriously react with the acid or the alcohol in the composition.

The virucidal compositions of this invention may also be used to prevent the spread of infection by viruses that reside in and/or are transmitted by and/or infect the cells of the dermis or epidermis. That is, in another embodiment of this invention the compositions of this invention may be incorporated into a hand cream or lotion for use by medical personnel both before and after the examination of patients with suspected virus infections. The compositions of this invention may be used in fluids used to kill virus on examining tables, instruments, gloves, towels and other surfaces which might come in contact with virus particles during the course of medical examinations. Further, all of the ingredients employed in the compositions of this invention are generally recognized as safe. The low toxicity of the compounds of the invention further enhances their attractiveness for such prophylactic use.

EXAMPLE 1

Growth Inhibition of HSV-1 In vitro Using Various Alcohol Concentrations at pH 3.5

The following ethanol solutions were made by diluting 95% ethanol with Eagles medium (pH14.2):1%, 2.5%, 5%, 10%, and 12.5%. The pH was adjusted with 0.1N HCl or 1.0N HCl to pH 3.5. Each solution was also diluted by ¼, ¹⁄₁₆ and ¹⁄₆₄ with Eagles medium as shown in Table 1.

The assay was performed upon Vero African green monkey kidney cells that have been grown in polypropylene 12-well trays in Eagles minimum essential nutrient medium containing 5% fetal bovine serum. The trays were incubated until a monolayer of cells had fully grown across the bottom of the tray. Each tray slot contains approximately 2 mL of Eagles medium adjusted to a pH of 7.

The virus was collected from a subject with an active Herpes Type 1 lesion. The sample was inoculated into a flask containing Vero cells grown in Eagles medium, pH 7.3. After the virus had infected all cells, the flask was frozen and thawed several times to burst the cells and release the virus. The contents were centrifuged to remove the cellular debris and the supernatant containing the virus was dispensed into ampules and stored at −20° C. for short term storage. One thawed virus ampule was diluted in Eagles medium, pH 7.3, so that 0.25 mL contained sufficient virus to form 25–50 plaques per well in the virus controls.

The alcohol solution to be tested for activity was dissolved in Eagles medium, adjusted to pH 4, then serially diluted ¼, ¹⁄₁₆, ¹⁄₆₄, etc. in Eagles medium. Virus was added, 0.25 mL per sample dilution, and held for the specified period. Two drops from a Pasteur pipette were then added to each of two wells in the plate. After 3 days of incubation, the wells were examined for cytopathic effect. Control wells typically show 25–50 plaques.

EXAMPLE 2

In vivo Inhibition of HSV-1

Three human subjects having history of acute recurrence of herpes labialis with a reported average duration of untreated episodes lasting ten days applied a solution prepared by combining 10 mL of 95% ethanol, 0.6 g glycolic acid, and 90 mL distilled water, wherein the final pH of the solution was 2.45, to affected areas once every 20 minutes for a minimum of three times daily during a 24 hour period. The material was dabbed on by finger and allowed to air dry between applications. When applied at the time of erythema, papule or vesicle stages, development was arrested and rapid crusting of vesicles occurred. Complete healing occurred when the crust fell off spontaneously or there was no longer evidence of an active lesion. These data show that the duration of cold sores decreased significantly to an average of 2 days following the above-described treatment.

When the same composition was applied within 24 hours of awareness, i.e., burning, tingling or itching, further development did not occur. The usual edema and pain accompanying herpes eruptions was eliminated.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

We claim:

1. A method of inactivating a virus, said method comprising contacting said virus with a virucidally effective amount of a composition consisting of:
   a pharmaceutically acceptable carrier;
   a C1, a C2, or a C3 straight chain alcohol or a C2, C3, or C4 diol having a concentration of 0.2 to 13.0% by volume in water; and
   a sufficient amount of an acid to adjust the pH of the composition to a range from 2.45 and to 4.6, wherein said acid is an organic acid selected from the group consisting of glycolic acid, lactic acid, succinic acid, malic acid, citric acid and acetic acid, or an inorganic acid;
   wherein the combination of alcohol or diol and acid is synergistic providing greater virucidal activity than the alcohol used alone.

2. The method of claim 1, wherein said alcohol is selected from the group consisting of methanol, ethanol, 1-propanol, and 2-propanol.

3. The method of claim 1, wherein said alcohol is selected from the group consisting of 2,3-butanediol, 1,2-butanediol, 1,3-butanediol, and 1,4-butanediol.

4. The method of claim 2, wherein said alcohol is ethanol.

5. The method of claim 1, wherein said acid is an inorganic acid.

6. The method of claim 5, wherein said acid is hydrochloric acid.

7. The method of claim 1, wherein the pH of said composition is 2.45.

8. The method of claim 1, wherein said virus resides in the dermis or epidermis of a human or animal infected by said virus.

9. The method of claim 1, wherein said composition is applied topically to reduce or inhibit lesions in an animal or human suffering from an infection by said virus.

10. The method of claim 1, wherein said virus is a member of the Herpesviridae family.

11. The method of claim 10, wherein said virus is herpes simplex 1.

12. The method of claim 10, wherein said virus is herpes simplex 2.

13. The method of claim 1, wherein said virus is Varicella-zoster virus.

14. The method of claim 1, wherein said virus is a member of the Poxviridae family.

15. The method of claim 14, wherein said virus is molluscum contagiosum.

16. The method of claim 1, wherein said virus is selected from the group consisting of rhinoviruses, adenoviruses, enteroviruses, cornoviruses, respiratory syncytial viruses, influenza viruses and parainfluenza viruses.

17. The method of claim 1, wherein said composition is a preparation selected from the group consisting of a tincture, gel, ointment, cream, salve, lotion, lip balm, foam, spray and aerosol.

18. A method of inactivating a virus, said method comprising contacting said virus with a virucidally effective amount of a composition consisting of:
   a pharmaceutically acceptable carrier;
   an alcohol selected from the group consisting of methanol, ethanol, 1-propanol, 2-propanol, 2,3-butanediol, 1,2-butanediol, 1,3-butanediol, and 1,4-butanediol having a concentration of 0.2 to 13.0% by volume in water; and
   a sufficient amount of an acid to adjust the pH of the composition to a pH of from 2.45 to 4.6, wherein said acid is selected from the group consisting of glycolic acid, lactic acid, succinic acid, malic acid, citric acid, acetic acid, and hydrochloric acid.

19. The method of claim 18, wherein the pH of said composition is 2.45.

20. The method of claim 18, wherein said composition is applied topically to reduce or inhibit lesions in an animal or human suffering from an infection by said virus.

21. The method of claim 18, wherein said virus resides in the dermis or epidermis of a human or animal infected by said virus.

22. The method of claim 18, wherein said virus is a member of the Herpesviridae family.

23. The method of claim 22, wherein said virus is herpes simplex 1.

24. The method of claim 22, wherein said virus is herpes simplex 2.

25. The method of claim 22, wherein said virus is Varicella-zoster virus.

26. The method of claim 18, wherein said virus is a member of the Poxviridae family.

27. The method of claim 26, wherein said virus is molluscum contagiosum.

28. The method of claim 18, wherein said virus is selected from the group consisting of rhinoviruses, adenoviruses, enteroviruses, comoviruses, respiratory syncytial viruses, influenza viruses and parainfluenza viruses.

29. The method of claim 18, wherein said composition is a topical preparation selected from the group consisting of a tincture, gel, ointment, cream, salve, lotion, lip balm, foam, spray and aerosol.

* * * * *